United States Patent [19]

Hansen

[11] Patent Number: 5,218,101

[45] Date of Patent: Jun. 8, 1993

[54] LEADER SEQUENCE INDUCING A POST-TRANSLATIONAL MODIFICATION OF POLYPEPTIDES IN BACTERIA, AND GENE THEREFOR

[75] Inventor: J. Norman Hansen, Silver Spring, Md.

[73] Assignee: The University of Maryland, College Park, Md.

[21] Appl. No.: 214,959

[22] Filed: Jul. 5, 1988

[51] Int. Cl.$^5$ .............................................. C12N 15/31
[52] U.S. Cl. .................................. 536/23.7; 435/69.1; 935/47; 935/49
[58] Field of Search .................... 435/69.1, 69.2, 69.7, 435/69.8, 71.2, 91, 172.1, 172.3, 252.3, 252.31-252.35, 320, 320.1; 536/27; 530/300, 325, 326, 350; 935/11, 47, 49, 72

[56] References Cited

U.S. PATENT DOCUMENTS 4,716,115 12/1987 Gonzalez et al. ................ 435/172.3

OTHER PUBLICATIONS

Hurst et al.; Can. J. Microbiol. 17: 1379 (1971).
Nishio et al.; Biochem. Biophys. Res. Comm. 116: 751 (1983).
Banerjee et al.; J. Biol. Chem. 263: 9508 (1988).

*Primary Examiner*—James Martinell
*Attorney, Agent, or Firm*—Oblon, Spivak, McClelland, Maier & Neustadt

[57] ABSTRACT

The method by which polypeptides having residues other than the 20 common amino acids are made is established. A leader peptide sequence, and its gene, are identified which induce or assist post-translational modifications of Cys, Thr and Ser in prokaryotes. The leader sequence may be used to induce the presence of covalent bonding sites in polypeptides and can be expressed by either naturally occurring or artificial means.

3 Claims, 3 Drawing Sheets

```
                 12              24              36      a gat ca        60
        CCG GAC AGG AGT ATT TTA AGG AAG AGC TTC AAG AGT TAA ACA AAA GAT CAT GAG CTA CTA
                                                                    (-35)
             tta tat      g att cca_____(mRNA)                                   120
        TGA CAA GGA TTA TAT CTT TGG ATT CCA TAA CTA TGA ATC AAT GGA AGG GGA CGA AGC AGT
             (-10)        (+1)
                                144             156             168             180
        ACC TTT GCA GTA CGT TGG TTT GTT GGA TGG AGC TGT AGG TGT AGG CTT AGG GGT ATT AAA 192             204             216             228             240
        CAT GGA ATT AGG CTC AAA AAC AGA TTG GAC AAA AGC ATT ATT AAT TTA ATA AAA AAA GGA 252             264             276            (r.b.s.)
        AAA AAA TGA TAA AAT CTT GAT ATT TGT CTG TTA CTA TTT AGG TAT TGA AAG GAG GTG ACC
                                                                   sss sss s
        xxxxxxxxxxxxxxxxxxxxxxxxxxxxxxxxxxxxxxxxxxxxxxxxxxxxxxxxxxxxxxxxxxxxxxxxxxxxxx
        AAT ATG TCA AAG TTC GAT GAT TTC GAT TTG GAT GTT GTG AAA GTC TCT AAA CAA GAC TCA
            Met Ser Lys Phe Asp Asp Phe Asp Leu Asp Val Val Lys Val Ser Lys Gln Asp Ser
                                        (leader region)

xxxxxxxxxxxxxxxxxxxxx ---  --- TC- --- --T --G --C --- --G --C --C --G --A --C --T
        AAA ATC ACT CCG CAA TGG AAA AGT GAA TCA CTT TGT ACA CCA GGA TGT GTA ACT GGT GCA
        Lys Ile Thr Pro Gln Trp Lys Ser Glu Ser Leu Cys Thr Pro Gly Cys Val Thr Gly Ala
                              1   2   3   4   5   6   7   8   9  10  11  12  13  14  15
        C-- --G --A --- --T --G --G --- --G --A --C --T --- --- --- --- ---           480
        TTG CAA ACT TGC TTC CTT CAA ACA CTA ACT TGT AAC TGC AAA ATC TCT AAA TAA GTA AAA
        Leu Gln Thr Cys Phe Leu Gln Thr Leu Thr Cys Asn Cys Lys Ile Ser Lys
         16  17  18  19  20  21  22  23  24  25  26  27  28  29  30  31  32
                 492             504             516             528             540
        CCA TTA GCA TCA CCT TGC TCT GAC TCC TTG CAC TTC TGA GTG TTA TAC ATA CTT ATT TTC
                 552             564
        ATA GAG TCG GGA CAA GAA AAT GAA GTA AAA AAC GAC GGG TGT GAA AGA GTT TAT ATT CAC
                                                       (terminator)
        ____     612             624             636             648             660
        ACC CGT TTT TAT ATT CGG CTT TAA GGA GGA ACA CAA TTG TAG AAC GGA AGA ACG GTT ATT
                 672             684             696             708             720
        TTC GAT CAT GCG TTT TGA ATA ACA TTC CAA TAA AAA TTC CAG TCT CTT CCT CAA ATG CAG
                 732             744             756             768             780
        ACA AAG GAT GAA GGA CTT AAG GGT ACT TAC CAG GTT TTA TGG TTA AGA ATA TTT CTA AGA
                 792             804             816             828
        ACA TCA TAT TTT TTA TTA GGA AAT TAA TAA ATG AGA TTG ATC ACT CTA GA
```

*FIG. 2*

```
                12            24            36            48            60
AGTTGACGAATATTTAATAATTTTATTAATATCTTGATTTTCTAGTTCCTGAATAATATA
                72            84            96           108           120
GAGATAGGTTTATTGAGTCTTAGACATACTTGAATGACCTAGTCTTATAACTATACTGAC
               132           144           156           168           180
AATAGAAACATTAACAAATCTAAAACAGTCTTAATTCTATCTTGAGAAAGTATTGGTAAT
               192           204           216           228           240
AATATTATTGTCGATAACGCGAGCATAATAAACGGCTCTGATTAAATTCTGAAGTTTGTT
         252  ^   ^ <--5' end of nisin mRNA    288          xxx
AGATACAATGATTTCGTTCGAAGGAACTACAAAATAAATTATAAGGAGGCACTCAAAATG
                                               r.b.s.        MET xxxxxxxxxxxxxxxxxxxxxxxxxxxxxxxxxxxxxxxxxxxxxxxxxxxxxxxxxxxx
AGTACAAAAGATTTTAACTTGGATTTGGTATCTGTTTCGAAGAAAGATTCAGGTGCATCA
SerThrLysAspPheAsnLeuAspLeuValSerValSerLysLysAspSerGlyAlaSer xxxxxx--C----TC---C--T-TG--C-----G--C--C---------C-----------C
CCACGCATTACAAGTATTTCGCTATGTACAGCCGGTTGTAAAACAGGAGCTCTGATGGGT
ProArgIleThrSerIleSerLeuCysThrProGlyCysLysThrGlyAlaLeuMETGly
    1  2  3  4  5  6  7  8  9 10 11 12 13 14 15 16 17 18
  20-mer
--C--T-----------T--A--C-----CTC---C--T--GTCT--            480
TGTAACATGAAAACAGCAACTTGTCATTGTAGTATTCACGTAAGCAAATAACCAAATCAA
CysAsnMETLysThrAlaThrCysHisCysSerIleHisValSerLysTER
 19 20 21 22 23 24 25 26 27 28 29 30 31 32 33 34
      492  3' end of nisin mRNA-->
AGGATAGTATTTTGTTAGTTCAGACATGGATACTATCC
```

*FIG. 3*

LEADER SEQUENCE INDUCING A POST-TRANSLATIONAL MODIFICATION OF POLYPEPTIDES IN BACTERIA, AND GENE THEREFOR

BACKGROUND OF THE INVENTION

1. Field of the Invention

This invention pertains to the expression of proteins which require post-translational modification of their amino acid sequence before a mature form is reached. Such proteins exhibit amino acids other than the 20 common amino acids coded for by the conventional nucleic acids. Specifically, a leader peptide sequence is identified which can induce post-translational modification of specific amino acids when expressed in conjunction with the precursor polypeptide. Methods of forming improved compositions using this leader sequence are also addressed.

2. Background of the Prior Art

Polypeptides, including those having natural antibiotic activities, have been identified which comprise amino acids other than the 20 common acids specified by the genetic code, as the expression products of bacteria, and other organisms. The structure of two of the more important ones, nisin and subtilin are set forth in FIG. 1 of this application.

The presence in these polypeptides, and others, of the unusual amino acids lanthionine, β-methyllanthionine, D-alanine, dehydroalanine, and dehydrobutyrine clearly suggests that something other than ordinary protein biosynthesis directed by the genetic code is involved in the expression of the mature forms of these naturally occurring polypeptides. Nonetheless, research has demonstrated that the appearance of these polypeptides can be blocked by protein biosynthesis inhibitors. Hurst et al., Canadian Journal of Microbiology, 17, 1379-1384 (1971). It is also known that precursor peptides of the mature forms can be detected with antibodies against the mature peptide. Nishio et al., Biochemistry Biophysics Research Community, 116, 751-751 (1983). These observations, with other observations concerning nisin, subtilin and related proteins suggest a mechanism that involves primary biosynthesis of a precursor via a ribosomal mechanism, followed by post-translational modifications.

The activity of these proteins, and potential mutant variations thereof, are of sufficient commercial interest so as to generate substantial activity in the field of derived microorganisms containing foreign DNA fragments and coding for the protein's production. U.S. Pat. No. 4,716,115, issued to Gonzalez et al. is directed to just such a derived microorganism. However, the impossibility of obtaining a genetic sequence that codes directly for the mature protein, and the lack of information concerning the nature of the post-translational modification necessary to arrive at the mature protein, has prohibited the cloning of microorganisms containing the specific gene which encodes for these proteins, and perhaps more importantly, has frustrated attempts to produce random variants and site-specific mutated proteins, which quite probably can be arrived at having higher degrees of activity, or other enhanced properties.

Thus, it remains an object of the biotechnology field to arrive at a comprehensive understanding of the mechanism by which the mature forms of these unusual amino acid-containing polypeptides are made, and to develop an expression vehicle for incorporating a gene which will specifically encode for the production of these peptides and which is suitable for the transformation of commonly available bacteria.

SUMMARY OF THE INVENTION

The Applicants have identified gene leader sequences, which, when coupled with the gene encoding the precursor of a polypeptide, induces or participates in the post-translational modification of the precursor to obtain the mature form. The structure of the full gene, including probable ribosomal binding sites, confirms the post-translational modification model for the manufacture of these peptides.

The gene for the expression of the precursor, and ultimately, the mature protein, of subtilin appears in FIG. 2. The leader sequence, which can be used to promote post-translational modification of other proteins which contain unusual amino acids, such as nisin and the like, is set forth specifically in FIG. 3. A separate leader sequence, bearing significant homology with that for subtilin, is also identified, and the overall gene sequence is given in FIG. 3.

BRIEF DESCRIPTION OF THE DRAWINGS

FIG. 2 is the genetic base pair sequence for the entire digested fragment containing the gene which encodes for the subtilin precursor peptide, including the leader fragment responsible for inducing post-translational modification. A putative ribosomal binding site is labeled R.B.S., the leader fragment has asterisks above it, and those amino acids of the precursor which undergo modification are set forth in bold face.

FIG. 3 is an illustration giving the sequence for the gene coding for nisin, and the precursor polypeptide corresponding thereto bearing the same types of markings and having the same meanings as FIG. 2.

DETAILED DESCRIPTION OF THE INVENTION

Figure 1:
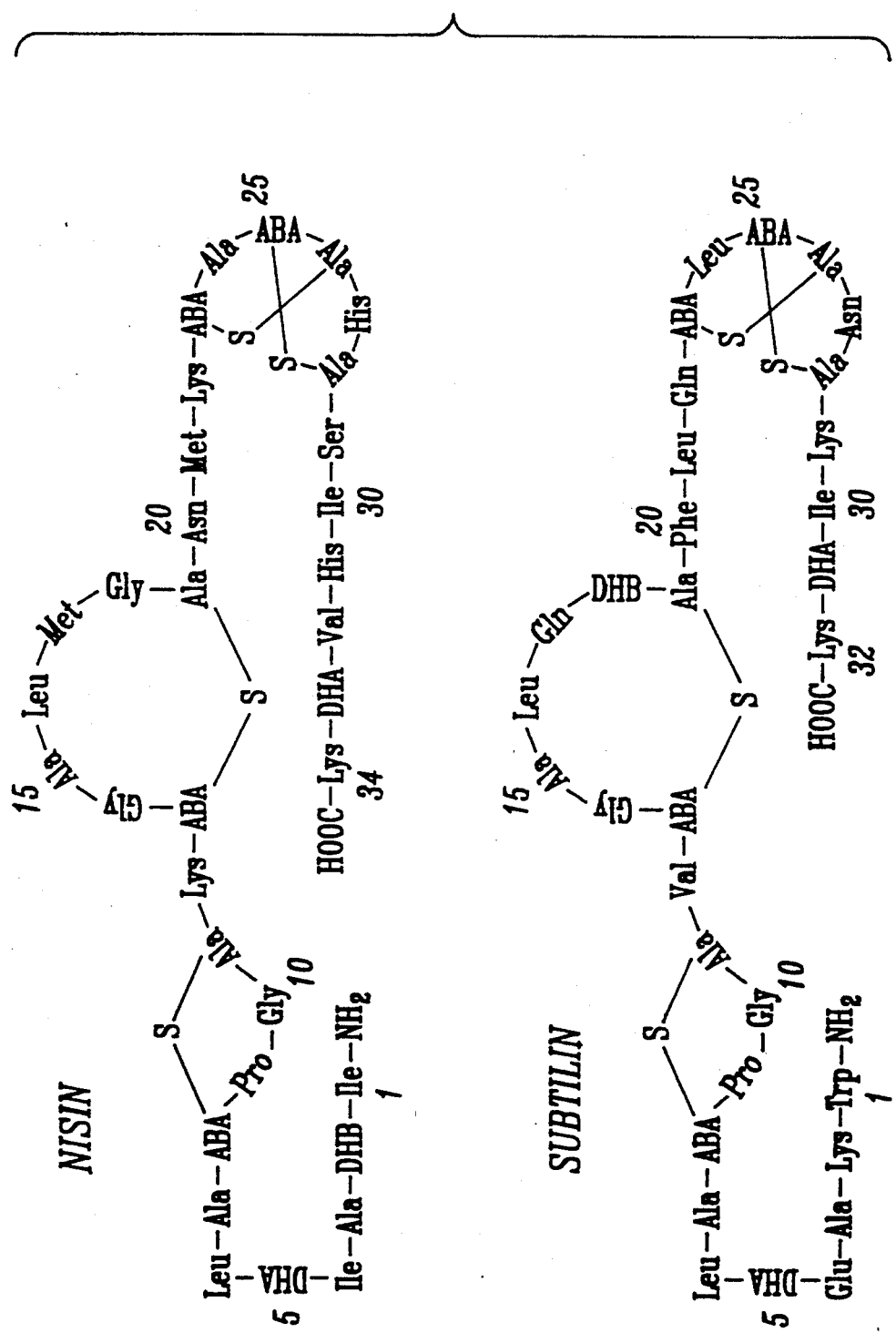
FIG. 1 is the conformational structure for the small antibiotic proteins nisin and subtilin, as determined by Gross et al., Protein Cross-linking, pages 131-153 (1977).

To arrive at the gene for the polypeptide precursor for the proteins of interest, and therefore, for the ultimate expression of the mature form of the protein, it is necessary to develop a gene probe, based on the putative amino acid precursor sequence of the protein in question. For ease of discussion, the description herein will be first in the context of the gene and precursor for subtilin, although the same methodology has been employed to determine the full gene for the precursor of nisin, as is discussed subsequently and is applicable to additional genes encoding proteins containing similarily unusual amino acids in the mature form as well.

SUBTILIN

Organism and Culture Conditions

Bacillus subtilis ATCC 6633, a subtilin-producing strain, was obtained from the American Type Culture Collection, Rockville, Md. It was cultured in the high-sucrose Medium A of Nishio et al (1983), originally described by Feeney et al (1948). It contains (per 1) 100 g sucrose, 11.7 g citric acid, 4 g $Na_2SO_4$, 4.2 g $(NH_4)_2HPO_4$, 5 g yeast extract (Difco), 100 ml of a salt mixture (7.62 g KCl, 4.18 g $MgCl_2$—$6H_2O$, 0.543 g MnCl$_2$—4H$_2$O), 0.49 g FeCl$_3$—6H$_2$O, and 0.208 g ZnCl$_2$ in 1,000 ml of H$_2$O), and sufficient NH$_4$OH to bring the pH to 6.8-6.9 per liter. Stocks were maintained on LB plates (10 g tryptone, 5 g yeast extract, 10 g NaCl per 1) containing 1.5% agar.

Clone Isolation and Hybridization Procedures

A subtilin gene probe was designed based on the putative amino acid precursor sequence of subtilin. The mature subtilin molecule contains only 32 amino acids, and does not contain any regions of low codon degeneracy. Therefore, instead of preparing a probe mixture which contained all possible sequences encoding a short stretch of amino acids in the subtilin precursor, a single long probe was synthesized according to the strategy of Lathe, Journal of Molecular Biology, 183, pp. 1-12 (1985). Ambiguous positions within codons were chosen by educated guess, according to a codon frequency usage table constructed from the known B. subtilis gene which codes for alpha-amylase Yang et al, Nucleic Acids Research, 11, pp. 237-249 (1983). Because one cannot predict the sequence homology between the probe and the target gene sequence, hybridization and wash conditions must be optimized emperically. The 96-mer "guessmer" was end-labeled using polynucleotide kinase, purified on disulfide cross-linked BAC gels as described by Hansen et al (1982), and hybridized to EcoRl digests of total ATCC 6633 genomic DNA at 7° C. temperature intervals in the range of 37-60° C., using a 6×Standard Saline Citrate (SSC) salt strength. Separate strips were then washed, using temperature increments of 4° C., in 2×SSC. The hybridization and wash conditions that gave the best combination of signal strength and specificity were chosen for subsequent screening of a partial Mbol library of ATCC 6633 DNA constructed in lambda J1. Hybridizations in which probe and target were highly homologous were carried out in the same hybridization buffer as above, but the hybridization temperature was 70° C., washes were done in 0.1×SSC at 52° C. DNA sequence analysis was done using the modified T7 polymerase "Sequenase" system suppled by United States Biochemical Corp.

RNA Isolation and S1-Mapping

Total RNA was isolated using the method of Ulmanen et al (1985). S1-mapping was performed by the method of Davis et al (1986), in which a synthetic oligonucleotide is used to prime second strand sythesis using single-strand M13 DNA which contains the cloned gene as template. Label was incorporated as $^{32}$P from [alpha-$^{32}$P-dATP]. After a short labeling time, an excess of unlabeled dATP was added, and second strand synthesis was continued toward completion. An appropriate restriction enzyme was used to cut the double-stranded product, and the labeled strand was obtained by electrophoresis on a denaturing agarose gel, followed by autoradiography to locate the fragment, excision of the gel, and electroelution of the DNA. After electroelution, the DNA was extracted with 1:1 chloroform:phenol and precipitated with ethanol. The labeled fragment was hybridized to total mRNA at several different temperatures, and unhybridized single-strand nucleic acid was degraded using nuclease-S1. The product was electrophoresed on a denaturing sequencing gel alongside a set of dideoxy sequencing reactions generated using the same synthetic oligonucleotide as primer. The location of the protected labeled DNA fragment with respect to the sequencing lanes identified the end of the mRNA.

RNA and Protein Analysis

Northern analysis was done by electroblotting acrylamide gels of RNA preparations onto Zeta-probe nylon membrane (Bio-Rad). Proteins were analyzed by electrophoresis on the polyacrylamide gel system of Swank and Munkres (1971), and silver-stained using Bio-Rad reagents. Subtilin activity was measured as for nisin, described by Morris et al (1984).

Using the above materials and methods, fragments which contained the sequence hybridizing with the guessmer were cloned into M13 and sequenced. The sequence was searched for homology to the subtilis gene probe, and also computer-translated in all reading frames. These were searched for the putative subtilin precursor sequence. A perfect match was found, which contains the exact sequence of 32 residues. The sequence is set forth in FIG. 3.

As noted, this sequence includes a portion encoding a precursor polypeptide, which contains serines, threonines and cysteines which undergo modification after translation, to arrive at the mature protein, having the unusual amino acids noted. The (−10) region corresponds closely to a consensus prokaryotic promoter (TATAAT) as observed in other bacteria, Siebenlist et al., Cell, 20, pages 269-281 (1980). The putative ribosome binding site is labeled as RBS and encompasses a 12 base pair sequence that is typical of those observed in B. subtilis, as reported by Band et al., DNA, 3, pages 17-21 (1984). It should be noted that it is positioned so that translation initiation would begin at the immediate downstream Met codon, which initiates the leader sequence of this invention. It should be noted that the subtilin precursor peptide leader region, which plays a role in the transport of subtilin outside the cell, is unusual in comparison to sequences of other prokaryotic exported proteins.

NISIN

The above approach has been duplicated for the antibiotic nisin, and the resulting gene sequence, coding for the precursor, is set forth in FIG. 3 attached hereto.

Bacterial Strains, Cloning Vectors, and Culture Conditions

Nisin-producing Streptococcus lactis ATCC 11454 was obtained from the American Type Culture Collection (Rockville, Md.). Strains were stored at −20° C. in ATCC Medium 17 (100 g skim milk powder, 100 g tomato juice, 5 g yeast extract to pH 7.0) containing 25% glycerol. Working stocks were maintained on 1.2% LB agar plates (10 g Bacto-tryptone, 5 g Bacto-yeast extract, 10 g NaCl per liter). M17 culture medium (8), consisting of 5 g Bacto-peptone (Difco), 5 g Bacto-soytone (Difco), 2.5 g yeast extract (Difco), 5 g beef extract (Difco), 0.5 g ascorbic acid, 5 g lactose (or glucose) 19 g beta-disodium glycerophosphate (Eastman), and 0.12 g anhydrous MgSO$_4$ per liter, was used to culture S. lactis for nisin production, genomic library construction, and total RNA isolation. The organism was grown at 32° C. without aeration using a 2% inoculum into an appropriate volume of M17 medium.

Bacillus cereus T spores used in the assay for nisin production were prepared and stored as described in the art. Antibiotic activity assays were performed as previ-

DNA Isolation Procedure

S. lactis ATCC 11454 was incubated in 500 ml of M17 medium for 30 hours at 32° C. without aeration. Cells were collected by centrifugation, and washed in 25 ml PBS (8 g NaCl, 1.4 g Na$_2$HPO$_4$, 1.2 ml 1 N HCl per liter). The cells were resuspended in 15 ml 50 mM Tris-HCl (pH 7.6) and subsequently digested with 33 micrograms per ml mutanolysin (Sigma) for 15 minutes at 37° C. with gentle agitation (12). Then 5 ml of STEP solution (13) (0.5% SDS, 50 mM Tris-HCl in 0.4 M EDTA, and 1 mg per ml proteinase K) was added and incubation performed at 37° C. for 30 min with occasional mixing. The mixture was extracted with 1 volume of CHCl$_3$, 1 volume 50:50 phenol:CHCl$_3$, and finally with 1 volume CHCl$_3$. One-tenth volume 3 M Na acetate and 2 volumes ethanol were added; the DNA was spooled, and resuspended in 20 ml 50 mM Tris-HCl and 4 mM EDTA containing 50 micrograms per ml of pancreatic RNase (Sigma). The solution was dialyzed against a buffer of 50mM Tris-HCl and 4 mM EDTA for 16 hours at 4° C. with one buffer change. The DNA was ethanol-precipitated two times in the presence of 2.5 M ammonium acetate and finally dissolved in 2 ml 10 mM Tris-Hcl, pH 7.6.

Probe Construction, Radiolabeling, and Hybridization Procedures

Several different probes were used to search for the nisin gene in S. lactis ATCC 11454 DNA. Hybridization conditions were optimized as previously described (2). Two oligomeric probes were prepared by chemical synthesis using a Biosearch Model 8700 DNA synthesizer. One was a 20-mer mixed probe designed against a region of low codon degeneracy within the putative nisin precursor sequence. The second was a single sequence 103-mer oligonuceotide probe designed using the strategy of Lathe. A natural DNA probe was also employed, which was a 1.1 kb restriction fragment containing the subtilin gene that had previously been cloned from Bacillus subtilis ATCC 6633 (2).

Library Construction and Isolation of the nisin Gene

A total genomic library of S. lactis ATCC 11454 DNA in lambda J1 was constructed and screened as described above. Positive clones were mapped by restriction analysis and subcloned into pUC9 and pTZ19U plasmid vectors for further analysis, and into M13mp18 and M13mp18 for sequencing. Sequence determination was performed by the dideoxy termination method using modified T7 polymerase and the protocol in a Sequenase kit obtained from the United States Biochemical Company.

RNA Isolation and Northern Blot Analysis

Total RNA isolation was performed according to the method of Ulmanen et al. RNA fractionation was performed on a denaturing acrylamide gel, electroblotted onto Zeta-probe (Biorad) nylon membrane, and hybridized as described above.

Protein Analysis

Proteins were analyzed by electrophoresis on the polyacrylamide gel system of Swank and Munkres, and silver-stained using Bio-Rad reagents. Nisin activity was determined by the method of Morris et al. ously described using fractions of the S. lactis culture supernatant.

DISCUSSION

Thus, the mode by which subtilin, nisin, and other proteins containing unusual amino acids not encoded by the genetic code is established. Specific leader sequences encoded within the genes for subtilin and nisin shown in FIGS. 2 and 3 required for post-translational modification of specific amino acids, including precursor residues Ser, Thr and Cys, which are converted to the unusual amino acids referred above, undergoing reactions which include dehydration, and potential electrophilic addition reactions involving stereoinversion to generate thioether crosslinkages and D-amino acids. Genes coding for the precursor polypeptide, including the leader, can be inserted through conventional technologies into any expression vehicle, which, e.g., for nisin, include Streptococcus lactis as a natural producer, and the expression bacteria set forth, e.g., in U.S. Pat. No. 4,716,115. Similar expression vehicles can be identified for other proteins.

Subsequent to the invention addressed herein, the gene sequence for epidermin, another lanthionine-containing polypeptide antibiotic was published by Schnell et al, Nature, 333, pp. 276–278 (1988). Although the amino acid residues of the leader sequences for the three antibiotics reflect sufficient homology to indicate a common evolutionary origin, it is clear that at this time, there are significant differences in the amino acid sequences of each, and their corresponding gene sequences. However, the hydropathic index of the three leader amino acid sequences are astonishingly similar. Specifically, adjacent to the structural regions, there is a region of high hydrophilicity, followed by a region more distal from the structural region, which, on average, is neutral, but tends to alternate between a hydrophilic and a hydrophobic residue. Indeed, placed on the same graph, there is an amazing correlation with regard to these residues. This correlation continues down to the fact that each leader region reflects an interruption in the hydophilic residues with one hydrophobic residue, at the exact same location in each case. Thus, the invention herein embraces not only the recognition that modification is accomplished by encoding a leader region which directs or aids in achieving modification in the structural region, but extends to the recognition that the leader region can be generally characterized as having a portion proximal to the strucutral region which is hydrophilic in nature, complemented by a more distal portion wherein hydrophilic and hydrophobic residues alternate to give an overall neutral value. Emperically, the three examples set forth herein all include the presence of a single hydrophobic residue in the hydrophilic portion adjacent the structural region. As of the filing date of this application, it is unknown whether the presence of such a residue is essential for achieving the post-translational modifications necessary. However, given the state of skill in the art, routine experimentation can determine the necessity of such a presence, together with various alternatives, which may improve modification efficiency.

The available technology also allows the manufacture of a gene encoding a mature protein, from the gene for the structural region only, which in many cases can be determined in a relatively straightforward manner, i.e., prediction based on the amino acid sequence followed by hybridization and sequence analysis. The effect of the leader sequence of this invention on specific amino acids also provides a novel means for achieving site-specific mutagenesis without resort to DNA modification. Thus, for example, it has been reported that deletion or replacement of various residues, such as cysteine, may improve biological activity. See, e.g., U.S. Pat. No. 4,518,584. Additionally, novel mutants of naturally-occurring peptides are quite likely to possibly exhibit higher activities, or better specificities for certain biological functions. These can now be prepared by insertion of the genetic code for the leader sequence of this invention in front of the gene encoding the expression of a naturally-occurring polypeptide, which will then undergo the post-translational modification directed by the leader sequence, eliminating or modifying the residues in question.

It should also be noted, of course, that where it is desired to secure substantial expression of the precursor, and not the peptide itself, this can now also be achieved, by specific excision of the leader fragment from the gene encoding the peptide precursor. In the absence of the leader sequence of this invention, it is the precursor which will be expressed, without direction to undergo post-translational modification.

Another feature of the invention of this application is the capability of designing "targeted proteins", or proteins which, by virtue of the presence of the unusual amino acids dehydroalanine and dehydrobutyrine, can be covalently attached to a "target". Thus, using structural variants, which could recognize and select for specific targets, the leader fragment can be employed to induce "binding sites", to develop a covalent bonding "antibody", to neutralize specific toxins, to select out specific material, etc. All these modifications are well within the skill of the ordinary practitioner and the expanding biotechnology arts, and so represent immediate applications of the discovery of the leader sequence disclosed herein.

Applications of this invention are not limited to the modification of existing proteins. Given current abilities to synthesize DNA sequences, specific polypeptides can be encoded by artificial clones and targeted for specific uses. As an example, given the crosslinking ability of the unusual amino acids produced through this invention, an adhesive can be prepared specific for a given substrate, e.g., carbon fibres, which due to the capability of the unusual amino acids generated by modification to form covalent linkages, can firmly bond to the substrate. The availability of amino acids allows the designer to introduce as an adhesive any desired amount of hydrophobicity, hydrophilicity, etc., to overcome problems encountered in currently used adhesives, such as epoxies.

Of course, specific applications will generate mutations of the leader sequence of this invention, and other specific variants. So long as these variants retain the essential biological function of inducing or assisting in post-translational modification, they remain within the scope of this invention.

It should be noted that a publication detailing the identification of the leader sequence by the Applicant, in conjunction with Sharmila Banerjee will appear in the Journal of Biological Chemistry, Vol. 263, proposed publication date Jul. 5, 1988.

The exact mechanism by which post-translational modification is induced is unclear. Without being bound to any theory, it is noted that the subtilin precursor exhibits residues in the leader sequence that initially alternate between high hydrophilic and high hydrophobic nature, becoming highly hydrophilic near the structural region, which, in contrast is strongly hydrophobic. This should be contrasted with usual leader regions for exported proteins of prokaryotes, which generally have a quite hydrophobic region, and contain basic residues, not the acidic residues of the invention. This suggests the post-translational modifications occur at a compartmentalized site, which the unusual leader sequence assists in targeting or directing the precursor too. It is expected that other proteins will participate in the modification mechanisms. Enzymes necessary to effect the essential chemical reactions localized at or near the cell membrane.

This invention has been described in specific detail with regard to specific proteins, materials and methods. Except where necessary for operability, no limitation to these specific materials is intended, nor should such a limitation be apprehended, outside the express limitations of the claims appended hereto. In particular, use of the leader sequence of this invention in conjunction with virtually any prokaryotic expression vehicle, specifically bacteria, is contemplated.

What is claimed as new and desired to be secured by Letters Patent of the United States is:

1. A gene leader fragment encoding a peptide leader sequence which induces post-translational modification of amino acids selected from the group consisting of Cys, Ser and Thr, said fragment having the sequence ATG TCA AAG TTC GAT GAT TTC GAT TTG GAT GTT GTG AAA GTC TCT AAA CAA GAC TCA AAA ATC ACT CCG CAA.

2. A genetic sequence encoding a polypeptide precursor of subtilin in bacteria, having the sequence ATG TCA AAG TTC GAT GAT TTC GAT TTG GAT GTT GTG AAA GTC TCT AAA CAA GAC TCA AAA ATC ACT CCG CAA TGG AAA AGT GAA TCA CTT TGT ACA CCA GGA TGT GTA ACT GGT GCA TTG CAA ACT TGC TTC CTT CAA ACA CTA ACT TGT AAC TGC AAA ATC TCT AAA.

3. A gene leader fragment encoding a peptide leader sequence which induces post-translational modification of amino acids selected from the group consisting of Cys, Ser, and Thr, said fragment having the sequence ATG AGT ACA AAA GAT TTT AAC TTG GAT TTG GTA TCT GTT TCG AAG AAA GAT TCA GGT GCA TCA CCA CGC.

* * * * *